(12) United States Patent
Liu et al.

(10) Patent No.: US 9,913,700 B2
(45) Date of Patent: Mar. 13, 2018

(54) METHOD OF PRODUCING A POLYMER MATRIX

(71) Applicant: The Texas A&M University System, College Station, TX (US)

(72) Inventors: Xiaohua Liu, Plano, TX (US); Chi Ma, Dallas, TX (US); Tiejun Qu, Dallas, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 14/881,922

(22) Filed: Oct. 13, 2015

(65) Prior Publication Data

US 2016/0184058 A1 Jun. 30, 2016

Related U.S. Application Data

(60) Provisional application No. 62/063,334, filed on Oct. 13, 2014.

(51) Int. Cl.
| | |
|---|---|
| *B23K 26/55* | (2014.01) |
| *B29C 71/04* | (2006.01) |
| *A61C 8/02* | (2006.01) |
| *D01D 5/00* | (2006.01) |
| *B29C 69/00* | (2006.01) |
| *B23K 26/00* | (2014.01) |
| *A61C 8/00* | (2006.01) |

(52) U.S. Cl.
CPC .......... *A61C 8/0006* (2013.01); *A61C 8/0012* (2013.01); *B23K 26/006* (2013.01); *B29C 69/001* (2013.01); *D01D 5/003* (2013.01); *D01D 5/0023* (2013.01); *D01D 5/0038* (2013.01); *D01D 5/0076* (2013.01)

(58) Field of Classification Search
CPC .... B23K 26/006; B23K 26/55; B29C 69/001; B29C 71/04; D01D 5/0023; D01D 5/003; D01D 5/0038; D01D 5/0076
USPC .......................... 264/400, 464, 465, 466, 484
See application file for complete search history.

(56) References Cited

U.S. PATENT DOCUMENTS

| | | | | |
|---|---|---|---|---|
| 2006/0019389 A1* | 1/2006 | Yayon | ...................... | A01N 1/02 435/395 |
| 2009/0074832 A1* | 3/2009 | Zussman | .............. | D01D 5/0007 264/413 X |

\* cited by examiner

*Primary Examiner* — Leo B Tentoni
(74) *Attorney, Agent, or Firm* — Winstead PC

(57) ABSTRACT

The present invention relates to a biomimetic matrix for providing structural support and scaffolding that allows for regeneration of dentin, pulp, and periodontal tissues. A method of making the biomimetic matrix provides the ability to select both a size of a pore or tubule formed in the biomimetic matrix and a density of pores or tubules disposed throughout the biomimetic matrix. The present invention discloses an approach of successful tubular dentin regeneration both in vitro and in vivo using the biomimetic matrix.

6 Claims, 12 Drawing Sheets

METHOD OF PRODUCING A POLYMER MATRIX

CROSS-REFERENCES TO RELATED APPLICATIONS

This Application claims the benefit under 35 U.S.C. § 119(e) of U.S. Provisional Patent Application No. 62/063,334 filed Oct. 13, 2014 which is incorporated herein by reference in its entirety as if fully set forth herein.

STATEMENT REGARDING FEDERALLY-SPONSORED RESEARCH OR DEVELOPMENT

This invention was made with government support under DE022838 awarded by The National Institute of Dental and Craniofacial Research (National Institute of Health). The government has certain rights in the invention.

BACKGROUND OF THE INVENTION

Dental caries and periodontal diseases are among the most common chronic diseases affecting billions of people around the world. These two diseases are the leading cause of tooth loss which severely influences the quality of life of patients. Conventional approaches to treat those diseases do not perform biological repair or regeneration. Therefore, these treatments cannot fully recover the biological functions of normal teeth. Tissue engineering approaches have been introduced as an alternative strategy to restore lost tissues (dentin, pulp, periodontal ligament, etc.). This approach has an advantage over traditional strategies in that after healing, the damaged/lost tissues are restored to their original state. Clearly, regeneration is the most desirable outcome for any therapy. Significant progress of dental tissue regeneration has been made in recent years. However, the regeneration of well-organized dental tissues, which are crucial to perform their biological functions, has never been achieved. One of the main barriers is the difficulty of developing suitable biomaterials/matrix to guide cell growth, differentiation, and new tissue formation.

According to the National Institute of Dental and Craniofacial Research (NIDCR), dental caries and periodontal diseases affect 92% and 8.5%, respectively, of adults from 20 to 64 years old in USA. Current clinical treatments have various limitations and cannot fully recover the biological function of the original tooth. While tissue engineering strategies have been proven, the potential to regenerate functional dental tissues with the same structure of the natural dental counterparts has not been accomplished. Without the proper structure, the engineered tissue cannot fulfill its biological function.

SUMMARY OF THE INVENTION

The claimed invention is directed to a unique technology for preparing a biomimetic synthetic matrix that modulates the formation of well-ordered dental tissues in the same manner as natural tooth tissues. The technology is capable of precisely tailoring the physical architecture of the matrix including, the diameter of nanofibers, pore size, pore density and pore distribution. The formed synthetic matrix therefore, truly mimics natural dental extracellular matrix (ECM) and provides an excellent environment to guide the formation of well-organized dental tissue, including tubular dentin and periodontal ligaments. In summary, the technology is used to prepare biomimetic matrix and regenerate functional dental tissues; thereby, improving the life quality of patients who have lost/damaged dental tissues. The claimed invention is directed to the preparation of a synthetic biomimetic matrix which will be developed for clinical treatment to regenerate normal structured dental tissues for patients.

An embodiment of the invention is directed to a matrix comprising a layer having a predetermined porosity, wherein the layer is made of electrospun polymer fibers.

A further embodiment of the invention is directed to a method of producing a matrix, the method comprising: electrospinning a liquefied polymer onto an electrode hence providing a layer having a predetermined porosity. In certain embodiments of the invention, the precipitation electrode comprises a rotating mandrel.

In an embodiment of the invention, an electrospinning process is combined with laser ablation to create a porous matrix.

In an embodiment of the invention, the liquefied polymer is a biocompatible melted polymer.

An aspect of the invention is directed to a method of replacing a portion of a dental tissue, comprising: providing a porous matrix as described herein; and connecting the porous matrix to existing dental tissue.

In an embodiment of the claimed invention, the combination of electrospinning and laser ablation technology is used to synthesize a biomimetic matrix for well-ordered pulpodentin and periodontal tissue regeneration. Specifically, the electrospinning process is used to create a matrix layer and the laser ablation step is used to create the pores, or tubules, of a predetermined size in the matrix.

In an embodiment of the claimed invention, the porosity of the matrix changes along with the depth of the matrix.

In certain embodiments, the diameter of the pores of the matrix changes along the depth of the matrix. In some embodiments, the pores on the top surface of the matrix have a smaller diameter than the pores at the bottom surface of the matrix. In other embodiments, the pores on the bottom surface of the matrix have a smaller diameter than the pores on the top surface of the matrix. In certain embodiments, the pore size changes in a contiguous manner from the top of the matrix to the bottom of the matrix.

An embodiment of the claimed invention is further directed to a method to make new dental tissue comprising, applying dental stem cells onto a porous matrix and allowing the dental stem cells to develop into odontoblasts, wherein the dental stem cells comprise cells from an enamel organ and/or a pulp organ.

BRIEF DESCRIPTION OF THE DRAWINGS

For a more complete understanding of the present invention and for further objects and advantages thereof, reference may now be had to the following description taken in conjunction with the accompanying drawings in which.

DETAILED DESCRIPTION OF EXEMPLARY EMBODIMENTS

Various embodiments of the present invention will now be described more fully with reference to the accompanying drawings. The invention may, however, be embodied in many different forms and should not be construed as limited to the embodiments set forth herein.

Figure 1:
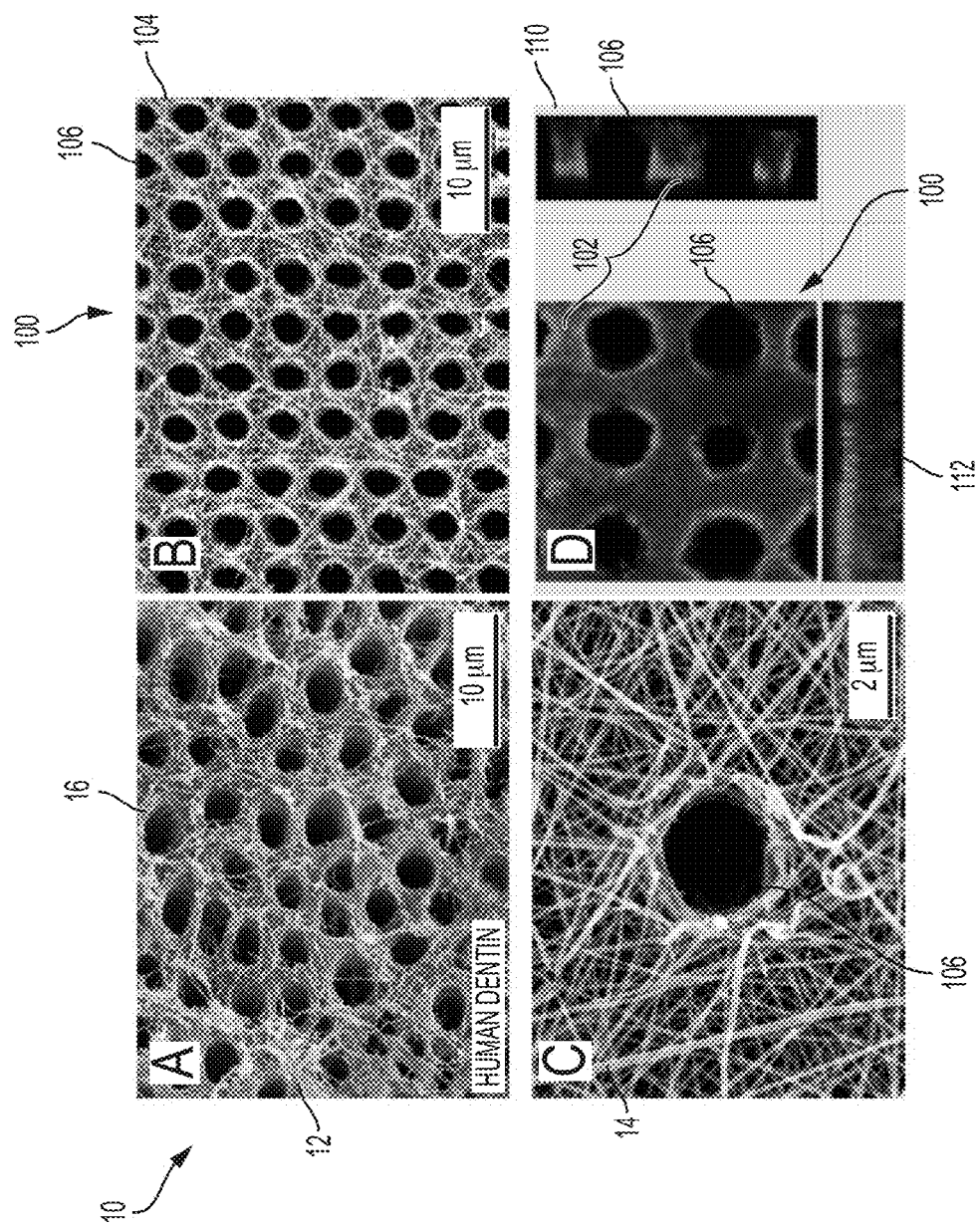
FIG. 1 depicts the following: (A) is an SEM image of a human-tubular matrix; (B) is an SEM image of a synthetic-tubular-gelatin matrix; (C) is a magnification of the image of FIG. 1A; and (D) is a confocal image of a synthetic-tubular-gelatin matrix.

FIG. 1A is a scanning electron microscope ("SEM") image of human dentin 10. The human dentin 10 includes a matrix 12 formed from a plurality of collagen fibers 14. The matrix 12 also includes a plurality of pores or tubules 16 formed through the matrix 12. FIG. 1B is an SEM image of a synthetic-tubular-gelatin matrix 100, which is a biomimetic matrix approximating the human dentin 10. The synthetic-tubular-gelatin matrix 100 comprises a matrix 102 formed from a plurality of gelatin nanofibers 104 (best seen in FIG. 1C). The gelatin nanofibers 104 mimic the collagen fibers 14 (the same range of size and almost the same chemical composition) of the human dentin 10. A plurality of tubules 106 are formed within the matrix 102. In one embodiment, the plurality of tubules 106 may be formed via laser ablation. The plurality of tubules 106 mimics the plurality of tubules 16. The plurality of tubules 106 can be formed at various distances from one another and with various diameters depending on various design considerations. In one embodiment, a diameter of one of the plurality of tubules 106 is approximately 2-3 μm, which is approximately the same diameter of the plurality of tubules 16. In certain embodiments, a diameter of one of the plurality of tubules 106 ranges from 2-5 μm. FIG. 1C is a magnification of an SEM image showing one of the plurality of tubules 106 formed in the plurality of gelatin nanofibers 104.

FIG. 1D is a confocal image of the synthetic-tubular-gelatin matrix 100, which shows a top view 108, a side view 110, and a side view 112 of the synthetic-tubular-gelatin matrix 100. The side view 110 shows that plurality of tubules 106 pass completely through the synthetic-tubular-gelatin matrix 100 and that diameters of the plurality of tubules 106 changes along a length of the plurality of tubules 106 (similar to that of plurality of tubules 16 from a near-pulp region to a dental-enamel junction "DEJ" region).

Figure 2:
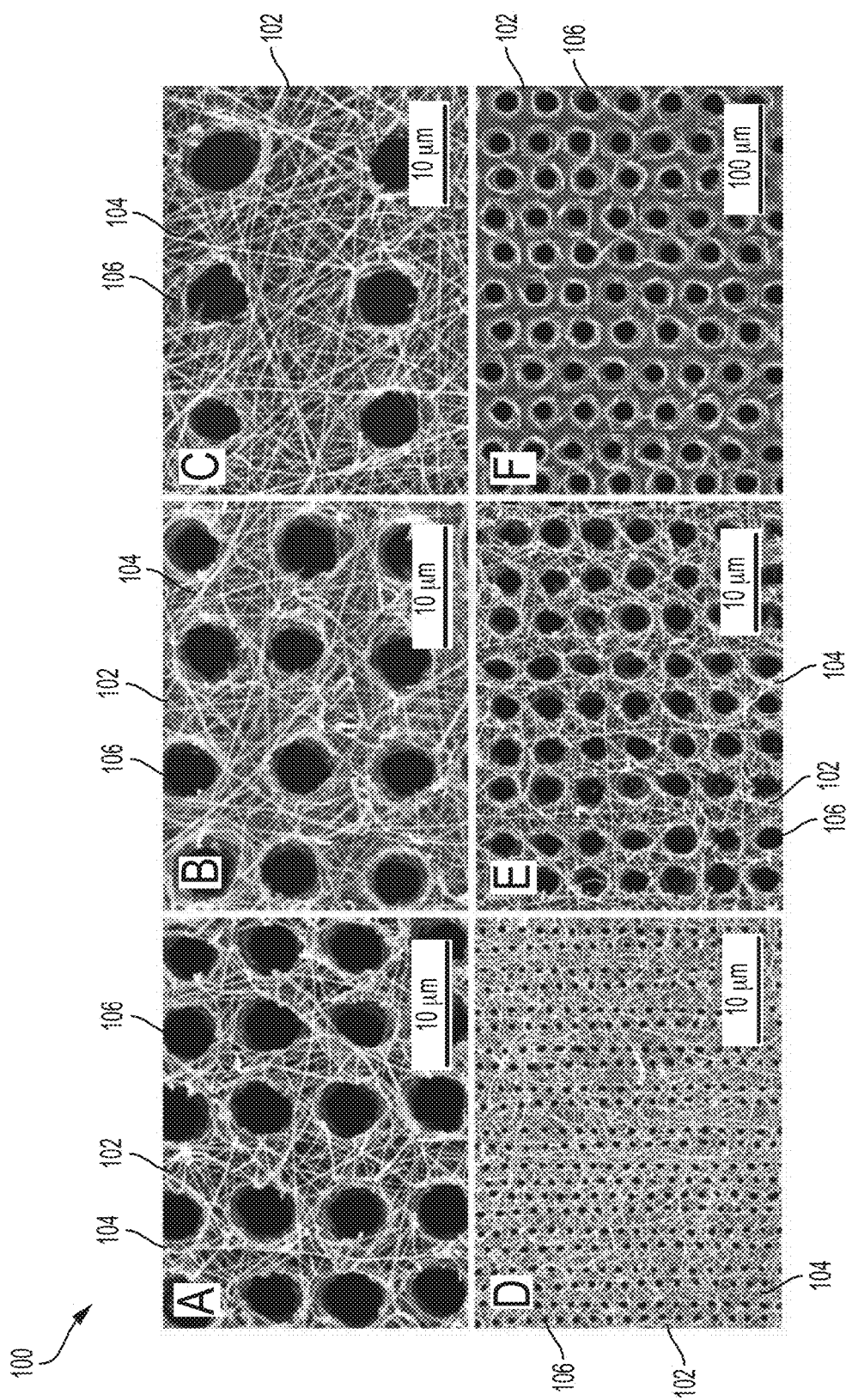
FIG. 2 shows multiple configurations (A to F) of a synthetic-tubular-gelatin matrix.

Referring now to FIGS. 2A-2F, control of a density of the plurality of tubules 106 and of a diameter of the plurality of tubules 106 is shown. FIGS. 2A-2C demonstrate that a tubular density—i.e., the number of tubules 106 per area—can be controlled. FIG. 2A depicts a relatively dense formation of tubules 106, while FIG. 2C depicts a relatively less dense formation of tubules 106. FIG. 2B depicts a density of tubules 106 between the densities shown in FIGS. 2A and 2C. The density of the tubules 106 may be varied in accordance with various design parameters. In addition to controlling the density of the tubules 106, the diameters of the tubules 106 may also be controlled as shown in FIGS. 2D-2F. As shown in FIGS. 2D-2F, the diameter of the tubules 106 may be varied between, for example, 300 nm and 30 μm. The diameter of the tubules 106 may be varied in accordance with various design parameters. In one embodiment, diameter variation is accomplished by manipulating, for example, an amount of time the laser is focused on the matrix 100, an amount of energy supplied to the matrix 100 by the laser, and the like.

Figure 3:
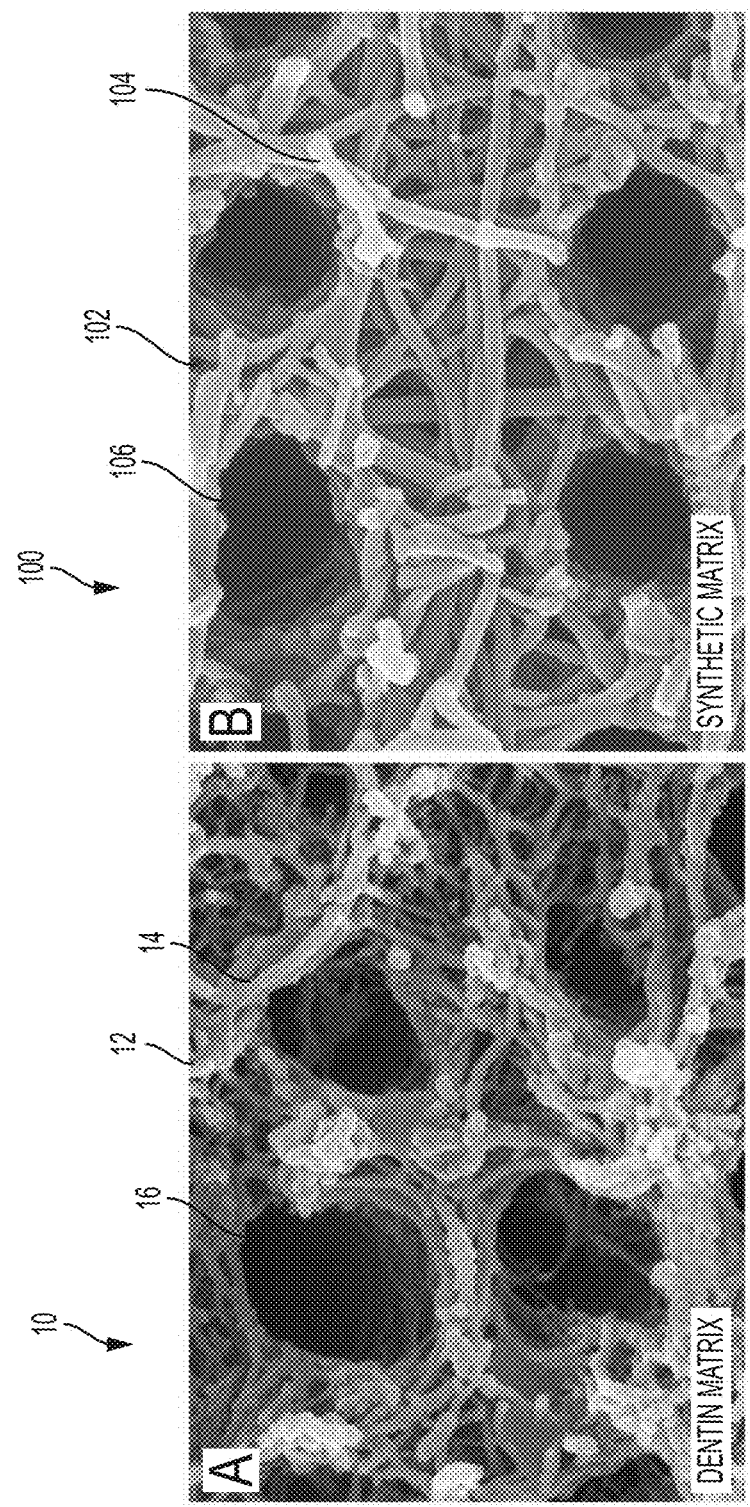
FIG. 3 depicts the following: (A) is an SEM image of a human dentin matrix; and (B) is an SEM image of a synthetic-tubular-gelatin matrix.

FIGS. 3A and 3B show SEM images of the human dentin 10 and the synthetic-tubular-gelatin matrix 100, respectively. As shown, the synthetic-tubular-gelatin matrix 100 mimics tubule diameter size, tubule gradient (i.e., a tapering of the tubule along its length, which results in a frustoconical shape), and tubule density.

Figure 4:
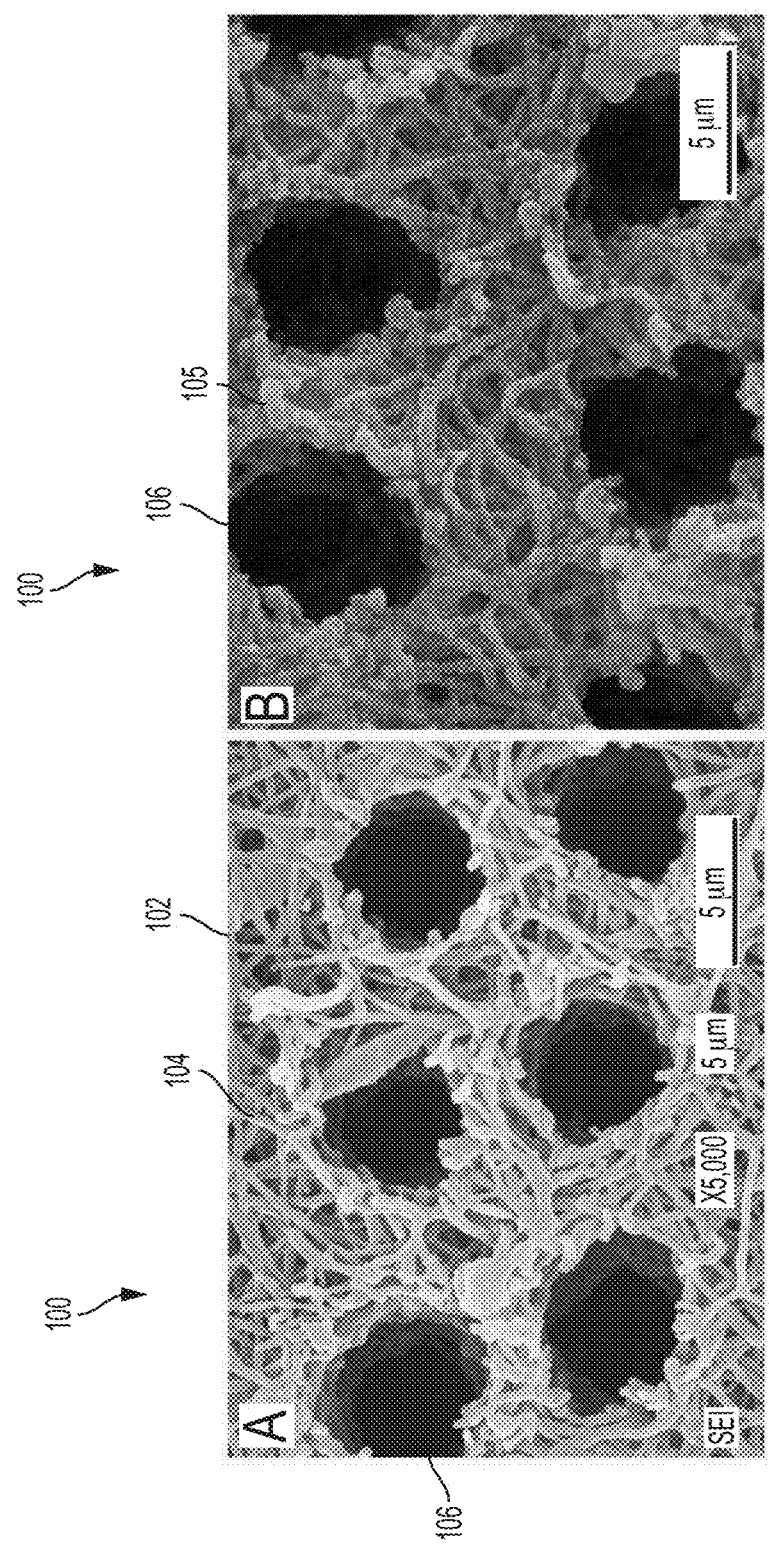
FIG. 4 shows SEM images of a synthetic-tubular-gelatin matrix (A) and a synthetic-tubular-matrix after mineralization (B), respectively.

FIGS. 4A and 4B show SEM images of the synthetic-tubular-gelatin matrix 100 before and after mineralization, respectively. As shown in FIG. 4B, the plurality of gelatin nanofibers have become mineralized nanofibers 105. The process of adding mineral to matrix is referred to as "mineralization."

Figure 5:
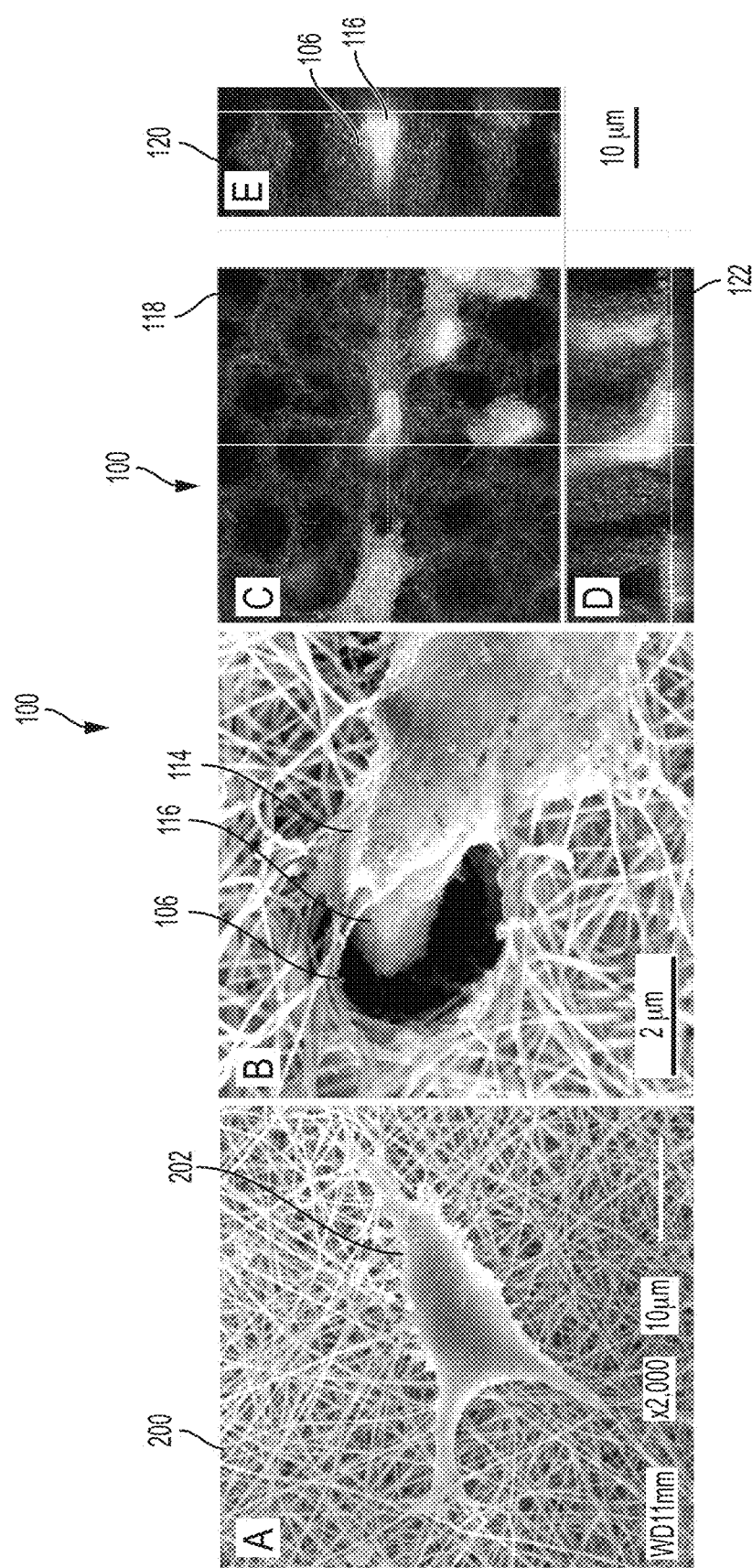
FIG. 5 depicts the following: (A) is an SEM image of a dental-pulp stem cell cultured on a synthetic-gelatin matrix without tubules; (B) is an SEM image of a dental-pulp stem cell cultured on a synthetic-tubular-gelatin matrix; (C), (D) and (E) are confocal images of dental-pulp stem cells on a synthetic-tubular-gelatin matrix after being cultured in a conditioned medium for 48 hours.

FIG. 5A shows a dental pulp stem cell ("DPSC") 202 cultured on a synthetic-gelatin matrix 200. The synthetic-gelatin matrix 200 differs from the synthetic-tubular-gelatin matrix 100 in that it does not include a plurality of tubules. FIG. 5B shows a DPSC 114 cultured on the synthetic-tubular-gelatin matrix 100. It is shown that a portion 116 of the DPSC 114 has descended into the tubule 106. As compared to DPSC 202, the DPSC 114 has obtained a superior attachment to the matrix.

FIGS. 5C, 5D and 5E are confocal images of the synthetic-tubular-gelatin matrix 100 of FIG. 5B. The lighter portion of the image in FIG. 5C depicts the DPSC 114. FIG. 5C shows a top view 118, FIG. 5E shows a side view 120, and FIG. 5D shows a side view 122 of the synthetic-tubular-gelatin matrix 100. As shown in the side view 120, the portion 116 of the DPSC 114 has descended into the tubule 106 to form a secure attachment to the synthetic-tubular-gelatin matrix 100.

Figure 6:
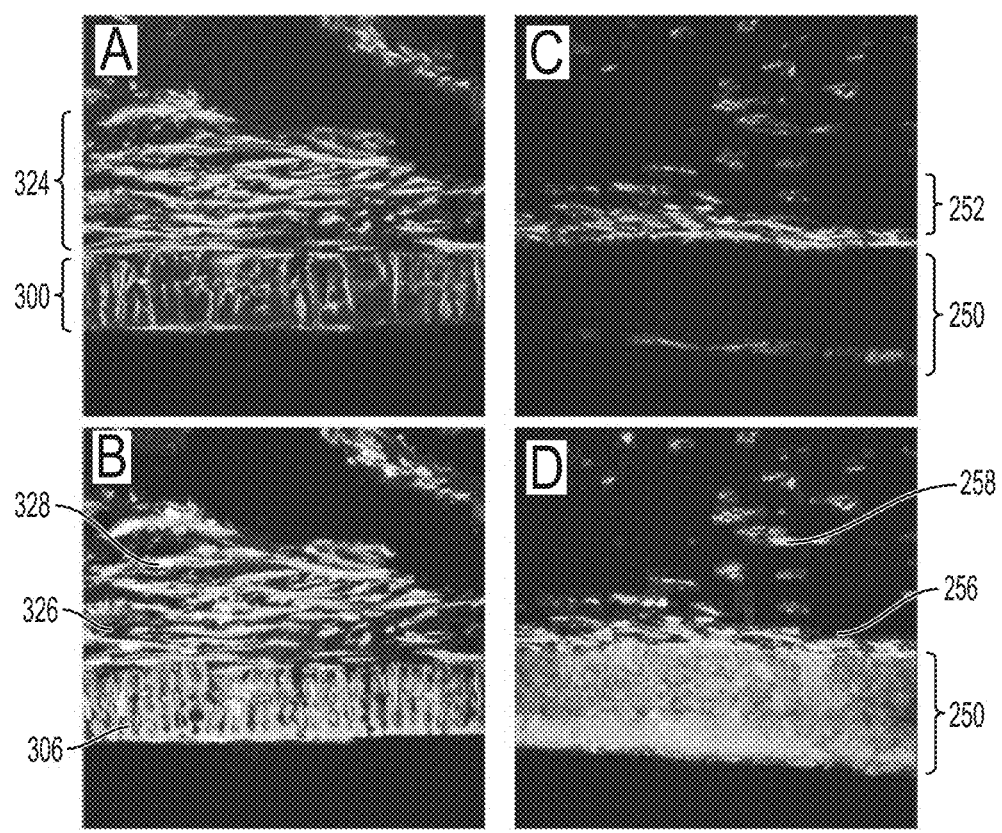
FIG. 6 shows cross-sectional views of dental-pulp stem cells cultured on a synthetic-tubular-gelatin matrix (A and B); and cross-sectional views of dental-pulp stem cells cultured on a synthetic-gelatin matrix without tubules (C and D)

FIG. 6A is a cross-sectional view of DPSCs 324 cultured on a synthetic-tubular-gelatin matrix 300. FIG. 6B is an enhanced view of FIG. 6A, where the synthetic-tubular gelatin matrix 300 has been highlighted to better show a matrix 302 and tubules 306, and the DBSCs 324 have been highlighted to better show F-actins 326 (shown as light gray layers stacked on top of the synthetic-tubular-gelatin matrix 300) and nuclei 328 (shown as bright spots within the light gray layers).

FIG. 6C is a cross-sectional view of DPSCs 352 cultured on a synthetic-gelatin matrix 350. FIG. 6D is an enhanced view of FIG. 6C, where the synthetic-gelatin matrix 350 has been highlighted to better show the matrix 350, and the DPSCs 352 have been highlighted to better show F-actins 356 (shown as light gray layers stacked on top of the synthetic-tubular-gelatin matrix 350) and nuclei 358 (shown as bright spots within the light gray layers). FIGS. 6A and 6B show a significant increase in DPSC 324 growth and a significant improvement in the interface between the DPSCs 324 and the synthetic-tubular-gelatin matrix as compared to the DPSCs 352 shown in FIGS. 6C and 6D.

Figure 7:
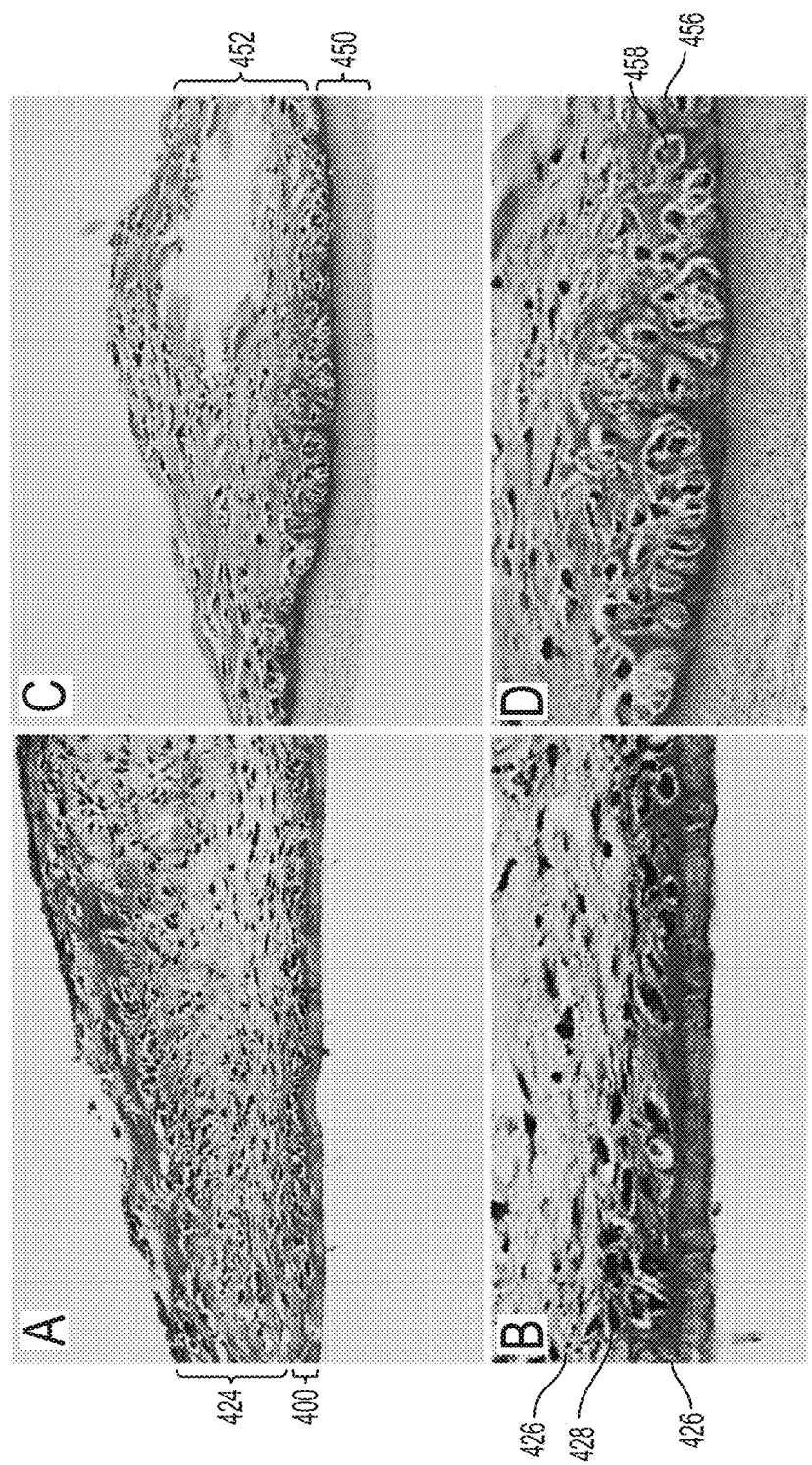
FIG. 7 shows side views showing regenerated tubular-dentin structure on a synthetic-tubular-gelatin matrix after in-vitro culture for two weeks (A and B); and side views showing regenerated tubular-dentin structure on a synthetic-gelatin matrix without tubules after in-vitro culture for two weeks (C and D)

FIG. 7A is a side view showing regenerated DPSCs 424 on a synthetic-tubular-gelatin matrix 400 after in-vitro culture for two weeks. FIG. 7B is a magnification of the image of FIG. 7A. F-actins 426 can be identified by the lighter gray colors of the image and nuclei 428 can be identified by the darker spots of the image. FIG. 7C is a side view showing regenerated DPSCs 452 on a synthetic-gelatin matrix 450 after in-vitro culture for two weeks. FIG. 7D is a magnification of the image of FIG. 7C. F-actins 456 can be identified by the lighter gray colors of the image and nuclei 458 can be identified by the darker spots of the image. FIGS. 7A and 7B show a significant increase in DPSC 424 growth and a significant improvement in the interface between the DPSCs 424 and the synthetic-tubular-gelatin matrix as compared to the DPSCs 452 shown in FIGS. 7C and 7D.

Figure 8:
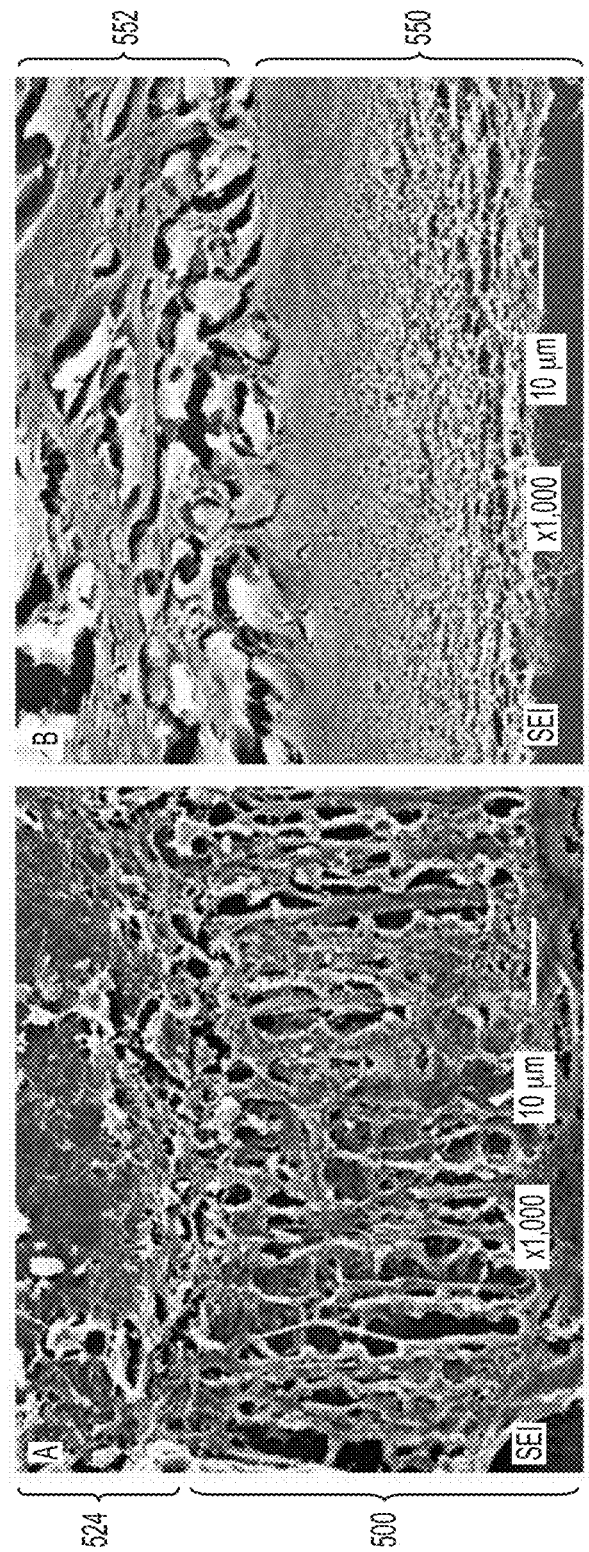
FIG. 8 shows an SEM image of dentin-pulp tissue cultured in vitro for two weeks on a synthetic-tubular-gelatin matrix (A); and an SEM image of dental-pulp tissue cultured in vitro for two weeks on a synthetic-gelatin matrix without tubules (B)

FIG. 8A is an SEM image of DPSCs 524 cultured in vitro for two weeks on a synthetic-tubular-gelatin matrix 500. FIG. 8B is an SEM image of DPSCs 552 cultured in vitro for two weeks on a synthetic-gelatin matrix 550. FIG. 8A shows an improved interface between the DPSCs 524 and the synthetic-tubular-gelatin matrix 500 as compared to an interface between the DPSCs 552 and the synthetic-gelatin matrix 550.

Figure 9:
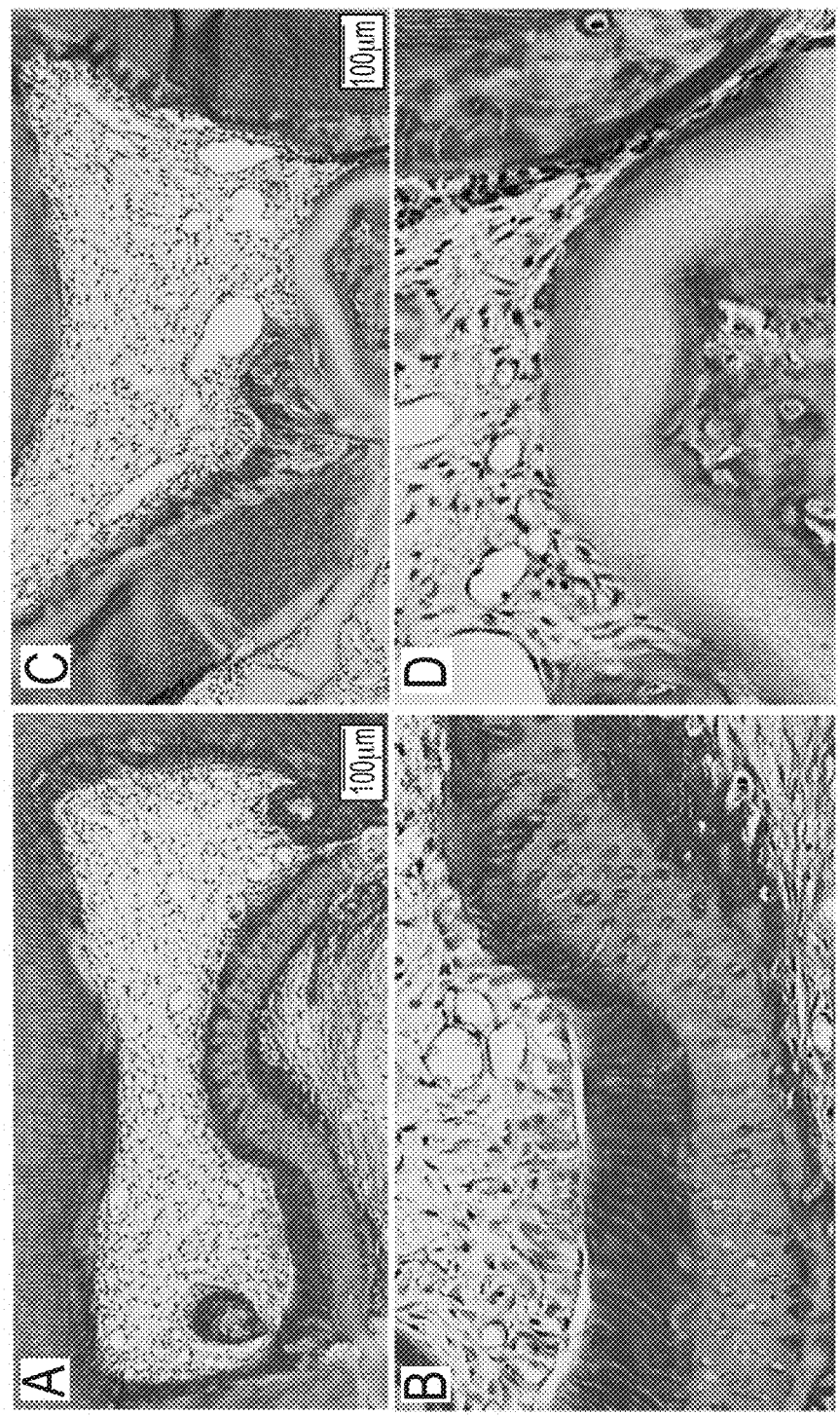
FIG. 9 shows side views showing regenerated tubular dentin and pulp tissues after in-vivo culturing for four weeks on a synthetic-tubular-gelatin matrix (A and B); and side views showing regenerated tubular dentin and pulp tissues after in vivo culturing for four weeks on a synthetic-gelatin matrix without tubules (C and D)

FIG. 9A shows regenerated DPSCs 624 after in-vivo culturing for four weeks on a synthetic-tubular-gelatin matrix 600. FIG. 9B is a magnification of the image in FIG. 9A. FIG. 9C shows regenerated DPSCs 552 after in-vivo culturing for four weeks on a synthetic-tubular-gelatin matrix 650. FIG. 9D is a magnification of the image in FIG. 9C.

Figure 10:
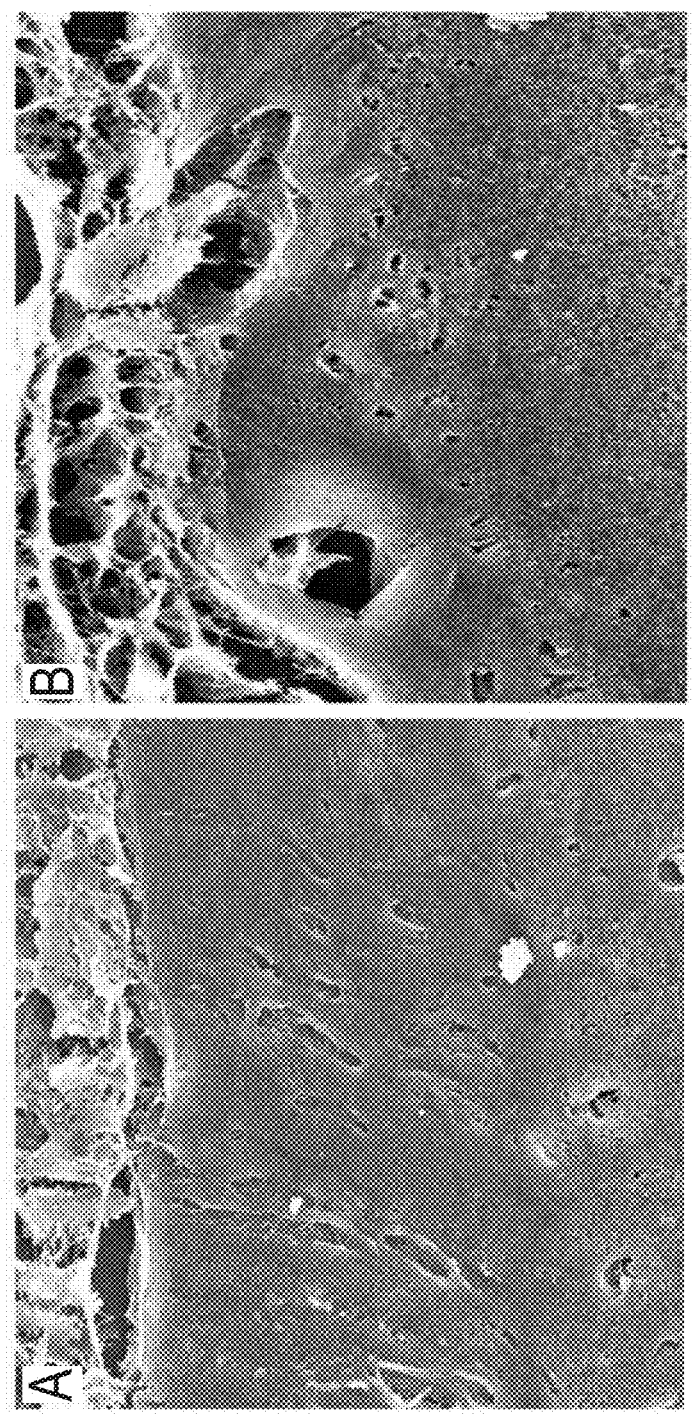
FIG. 10 shows SEM views of regenerated tissues after in-vivo culturing for four weeks on a synthetic-tubular-gelatin matrix (A) and a synthetic-gelatin matrix without tubules (B), respectively.

FIG. 10A is an SEM image showing regenerated DPSCs 724 after in-vivo culturing for four weeks on a synthetic-tubular-gelatin matrix 700. FIG. 10B is an SEM image showing regenerated DPSCs 752 after in-vivo culturing for four weeks on a synthetic-gelatin matrix 750.

Figure 11:
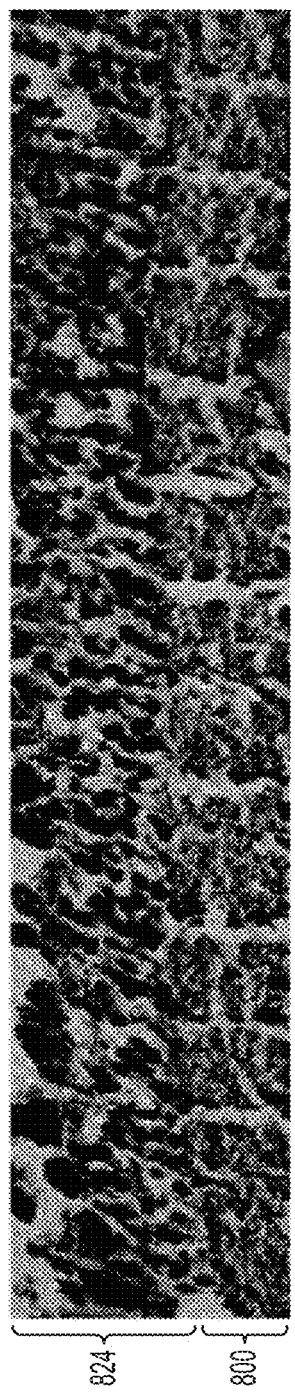
FIG. 11 shows Haemotoxylin and Eosin ("H&E") staining of dentin-pulp stem cells on a synthetic-tubular-gelatin matrix construct after being subcutaneously implanted into nude mice for 4 weeks.

FIG. 11 shows Haemotoxylin and Eosin ("H&E") staining of DPSCs 824 and a synthetic-tubular-gelatin matrix 800 after being subcutaneously implanted into nude mice for four weeks. A tubular dentin tissue was successfully regenerated, and odontoblasts were aligned in a well-organized way along the tubular matrix, similar to that of natural tubular dentin.

Figure 12:
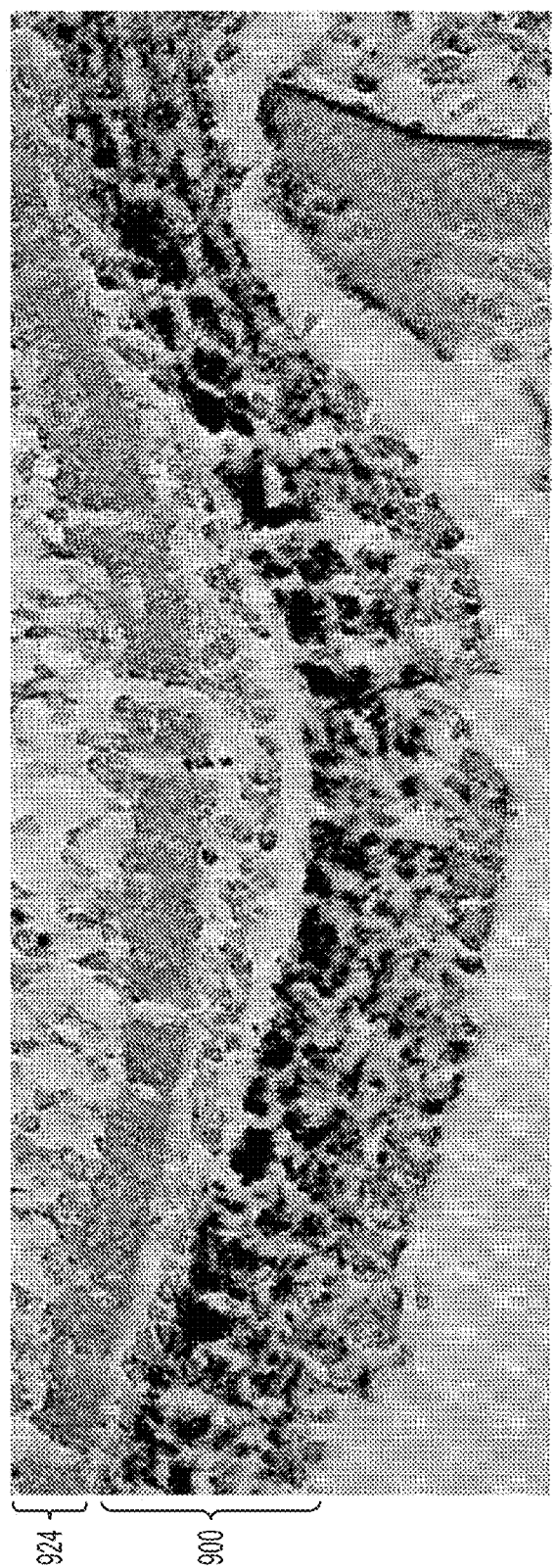
FIG. 12 shows von Kossa staining of dentin-pulp stem cells on a synthetic-tubular-gelatin matrix after being subcutaneously implanted into nude mice for four weeks.

FIG. 12 shows von Kossa staining of DPSCs 924 and a synthetic-tubular-gelatin matrix 900 after being subcutaneously implanted into nude mice for four weeks. A mineralized tubular dentin tissue was clearly observed from the von Kossa staining.

Working Examples

Nanofibrous synthetic matrix is fabricated by an electro-spinning process using a high-voltage power supplier (Model: ES30P-SW, Gamma High Voltage Research Inc.). The diameter of the matrix nanofiber was tailored by the polymer concentration and electrospinning speed. Next, a Leica Laser Microdissection 7000 (Leica microsystem, Germany) will be used to generate tubular structure on the nanofibrous matrix. The matrix will be tiled flat onto a glass coverslip. A software Leica laser microdissection V7.4.1 was used to design the pore distribution pattern. During the laser ablation process, the pore size was controlled by the laser aperture and laser pulse energy, and the pore density was modulated by the laser frequency and speed. For a typical experiment to generate the tubular architecture, the operation parameters of the equipment are as follows: laser aperture 30 Hz, laser pulse energy 30 Hz, laser speed 40 Hz, and laser pulse frequency 37 Hz. Using these parameters, more than 130000 tubular pores were created in each hour.

Increasing the pulse frequency increased the number of pores generated in each unit time. Because the laser strength is the highest on the top surface of the matrix and the lowest on the bottom of the matrix, an inverted cone-like structure of each cylindrical pore will be created during the laser ablation process. One advantage of using this technology is its capability to precisely relocate to its previous position; therefore, the ablation process can be repeated multiple times to ensure that each pore in the matrix is open. To prepare tubular matrix with different pore sizes and densities (optimization of the matrix), the operation parameters will be modulated in the following ranges: laser aperture 20-45, laser pulse energy 15-35, laser speed 5-100, and laser pulse frequency 10-65 Hz. The new technology has been developed and the biomimetic synthetic matrix has been prepared and optimized.

In the process, when the laser strength is highest on the top of the matrix, the pore size is larger on the top surface of the matrix relative to the bottom surface and progressively decreases in size along the depth of the matrix. However, it is desirable in certain situations to create a matrix having a pore size that is smaller on the top surface and larger on the bottom surface. In such situations, the bottom surface of the matrix is contacted with a glass substrate prior to exposing the top surface of the matrix to the laser. Contacting the bottom surface of the matrix with a glass substrate causes more heat to be generated on the bottom of the matrix than on the top surface, which in turn generates larger pores on the bottom of the matrix relative to the top surface of the matrix. Thus, using the processes of the claimed invention, it is possible to create a matrix having a continuously variable pore size along the depth of the matrix.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method of producing a polymer matrix, the method comprising:
   electrospinning a liquefied polymer onto an electrode to create a nanofibrous layer having a porosity; and
   ablating, via a laser, the layer to form a tubule through the layer; and
   wherein a diameter of the tubule changes along a depth of the nanofibrous layer.

2. The method of claim 1 wherein the electrode is a rotating mandrel.

3. The method of claim 1 wherein, the liquefied polymer is a biocompatible melted polymer.

4. The method of claim 1, wherein the porosity of the nanofibrous layer changes along a depth of the nanofibrous layer.

5. The method of claim 1, wherein the diameter of the tubule on a top surface of the polymer matrix is smaller than a diameter of the tubule on a bottom surface of the nanofibrous layer.

6. The method of claim 1, wherein the diameter changes in a contiguous manner from a first surface of the polymer matrix to a bottom surface of the polymer matrix.

\* \* \* \* \*